United States Patent
Hakky et al.

[11] Patent Number: 6,090,103
[45] Date of Patent: Jul. 18, 2000

[54] INTERSTITIAL LASER RESECTOSCOPE

[75] Inventors: Said I. Hakky; A-Hamid Hakki, both of Largo, Fla.

[73] Assignee: Canox International Ltd., Largo, Fla.

[21] Appl. No.: 09/107,374

[22] Filed: Jun. 30, 1998

[51] Int. Cl.$^7$ ............................. A61B 18/18; A61B 17/20
[52] U.S. Cl. ................................ 606/14; 606/15; 604/20; 604/22
[58] Field of Search .................. 606/10, 11, 12, 606/14, 15, 16, 17; 604/20, 21, 22

[56] References Cited

U.S. PATENT DOCUMENTS

| | | | |
|---|---|---|---|
| 4,306,557 | 12/1981 | North | 128/276 |
| 5,201,731 | 4/1993 | Hakky | 606/15 |
| 5,222,953 | 6/1993 | Dowlatshahi | 606/15 |
| 5,320,617 | 6/1994 | Leach | 606/15 |
| 5,425,355 | 6/1995 | Kulick | 606/15 |
| 5,498,258 | 3/1996 | Hakky et al. | 606/15 |
| 5,593,404 | 1/1997 | Costello et al. | 606/15 |
| 5,968,039 | 10/1999 | Deutsch et al. | 606/15 |

*Primary Examiner*—Linda C. M. Dvorak
*Assistant Examiner*—Sonya Harris Ogugua
*Attorney, Agent, or Firm*—Rosenberg, Klein & Lee

[57] ABSTRACT

The present invention provides a resectoscope and a method for lasing, coagulating, resecting, removing and retrieving prostate tissue. The resectoscope of the invention includes an interstitial laser fiber as a laser directing system and a unique configuration of an extensible and retractable plurality of thin blades which are capable of forming a plurality of elliptical shapes. Laser radiation sources are to be used with the device. This combination provides a more efficient and safer surgical method and provides the additional benefit without impairing the cellular integrity of the tissue. Thus, the retrieved tissue is preserved for histological analysis.

13 Claims, 3 Drawing Sheets

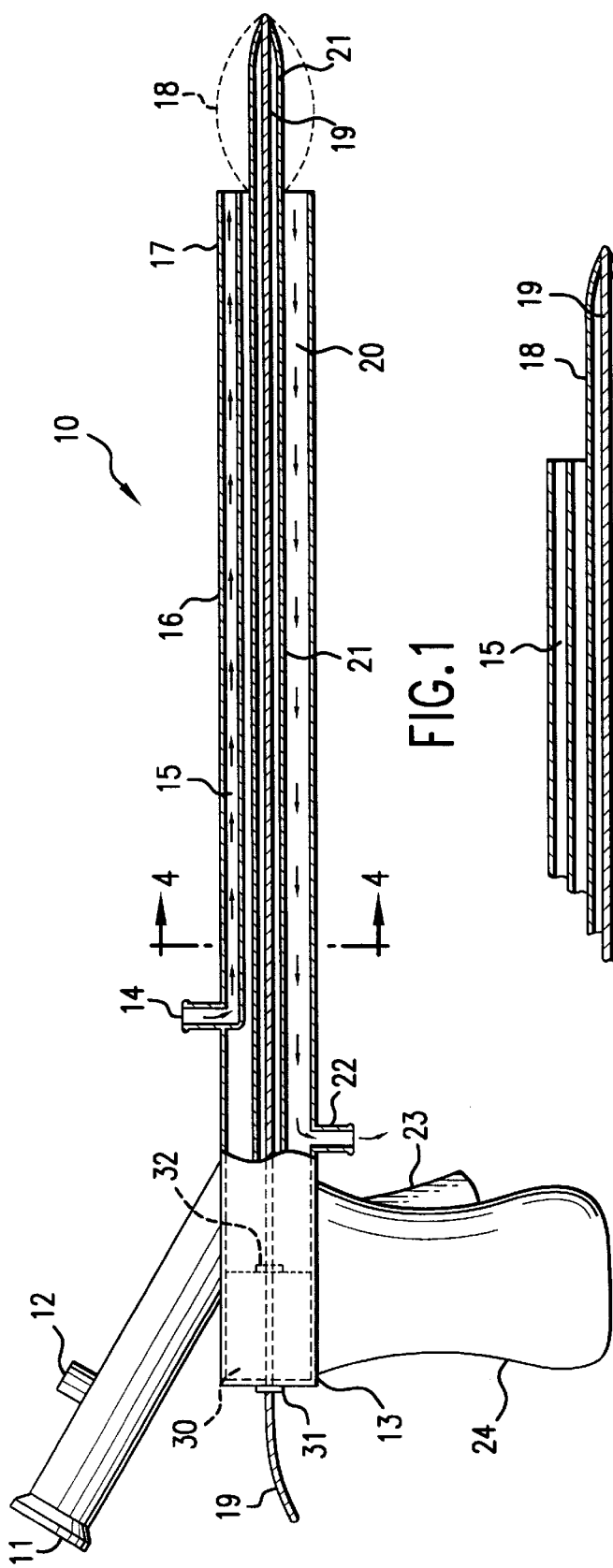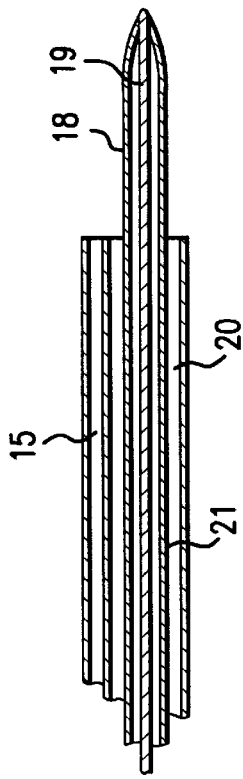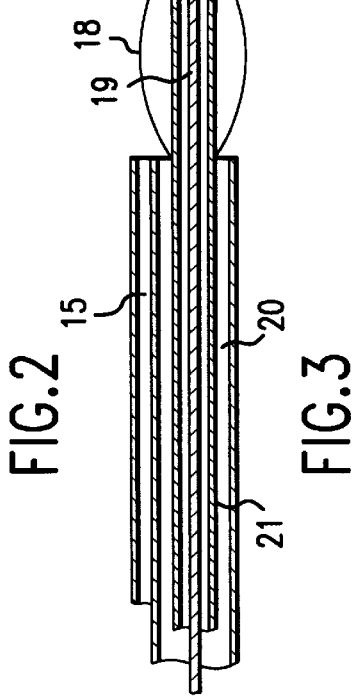

INTERSTITIAL LASER RESECTOSCOPE

BACKGROUND OF THE INVENTION

1. Field of the Invention

This invention relates generally to the field of surgical devices and more particularly to resectoscopes and methods for their use.

2. Discussion of the Prior Art

A resectoscope is employed transurethrally to perform prostate and/or bladder surgery. This device has an elongate central working section provided with an outer sheath, usually made of stainless steel, which is inserted into the urethra. The outer sheath prevents the urethra from collapsing, while the working elements internally of the sheath are employed to cut away the desired tissue.

In U.S. Pat. No. 4,955,882 there is disclosed a resectoscope instrument embodying a laser for use in coagulating and removing prostate tissue. A cutting blade is provided in that instrument for cutting away tissue which had been coagulated by the laser. To that end, the instrument utilizes a forward directed laser to penetrate the tissue to be removed prior to cutting of that tissue. The instrument also includes means by which an irrigation fluid can be continuously supplied to and removed from the cutting site, so that the irrigation fluid, cut tissue and any debris are withdrawn through the instrument without the need to fully irrigate the site.

Some devices are now becoming available for effecting transurethral resection of the prostate by means of a laser. For example, Surgical Laser Technologies of Oaks, Pa. offers a "contact laser" which serves to vaporize the prostate in order to reduce bleeding and morbidity common with the traditional transurethral resection techniques.

When performing a prostate resection (or other tissue resection procedures, for that matter) it is desirable to be able to retrieve the removed tissue for analysis, e.g., histological examination. Thus, laser devices which do not includes any means for effecting the retrieval of laser tissue, particularly with the cellular architecture of that tissue substantially preserved, leave much to be desired from the standpoint of patient care. For example, the use of such devices leaves open the possibility of the failure to detect pathological conditions, e.g., malignant cells, in the removed tissue.

In U.S. Pat. No. 5,312,399, entitled Laser Resectoscope With Mechanical Cutting Means and Laser Coagulating Means, issued to Hakky and Hudson, which disclosure is incorporated by reference herein, there is disclosed a laser resectoscope and method of use for coagulating and causing hemostasis in tissue, e.g., prostate tissue, of a living being and for effecting the removal of the coagulated tissue, while preserving the cellular structure of the removed tissue for subsequent examination. That resectoscope comprises an elongated member having a distal end portion for introduction, e.g., through an introducer sheath, into the patient adjacent the tissue to be removed. Laser means are provided at the distal end portion of the elongated member for producing and directing a laser beam into the adjacent tissue for coagulating at least a portion of it. A rotatable cutting means is also located at the distal end portion of the apparatus for removing at least a portion of the coagulated tissue and for carrying that removed tissue to means for retrieving it. The rotatable cutting means operates in such a manner that the cellular structure of the coagulated tissue removed by the cutter is substantially preserved and hence suitable for viable histological examination.

The control of the operation of a surgical laser, particularly of a laser resectoscope, is of considerable importance, since the laser beam is capable of destroying both healthy and diseased tissues. Thus, heretobefore the use of surgical lasers has been typically restricted to physicians who have undergone intensive training in their use so that such physicians are able to judge tissue reaction to the laser beam. For example, a laser beam delivered to living tissue produces protein denaturation at 40 to 65° C. At 65 to 85° C., a laser beam produces tissue coagulation. Tissues whose temperatures are raised to a temperature of 95 to 400° C., or more, vacuolizes, vaporizes or carbonizes, since a laser beam typically penetrates to a depth of between 0.5 to 4 millimeters below the surface of the tissue exposed to it.

Another concern in prostate and bladder resection is the removal of necrotic tissue and coagulated tissue which can avoid the use of a Foley catheter or shorten its use. The Foley catheter is used to divert the urine for many days from the prostate. This can cause irritation and possible infection.

Therefore, there exists a need for a laser resectoscope that efficiently removes tissue for diagnosis and necrotic tissue, and provides little risk regarding perforations of the prostatic urethra, rectum, or bladder.

There are many forms of laser applications. Laser energy can be applied using a fiber optic cable. The laser can be applied with the end tip of the fiber optic ("end lasing"). Here the laser beam fires from the tip of the fiber optic cable. The laser beam could also be deflected by a mirror so the beam will fire from the side of the fiber optic ("side firing"). In a new and novel laser application, Indigo Company in Cincinnati, a Johnson & Johnson Company, has devised an interstitial laser. The goal with an interstitial laser is to preserve the epithelial lining of the prostatic urethra and lase the core of the prostate surrounding a 2.5 centimeter segment of the fiber optic cable. In the interstitial laser, the end (5 centimeters) of the fiber optic is inserted inside the prostate (middle or the core of the prostate). Then laser energy is applied to the 2.5 centimeter tip of the fiber optic which is inside the prostatic core, and is uninsulated while the remaining fiber optic cable is insulated. Thus, when the laser energy is applied, the prostate tissue core surrounding the uninsulated 2.5 centimeter tip will be heated and thus be coagulated without damaging the overlying prostatic urethral lining. This interstitial laser application is meant to reduce the time the Foley catheter is left to divert the urine from the prostatic bed after the application of the laser.

Unfortunately, none of the above procedures remove coagulated or necrotic tissue. The lased prostate in all of the above is left to slough and pass with the urine over a period of 2 to 12 weeks. This can cause pain or discomfort during micturition. In addition, infection and scarring of the prostatic urethra mar the benefits of the laser.

SUMMARY OF THE INVENTION

In accordance with an aspect of the invention, a resectoscope and its method of use is disclosed for coagulating and causing hemostasis in prostate tissue of a living being and for effecting the removal of the coagulated tissue in such a manner that the cellular structure is preserved. Such preservation allows for a viable histological examination. The novel resectoscope comprises an elongated cylindrical member enclosing at least four conduits, with one including a rotating shaft which serves as a conduit for the interstitial laser fiber and carries the mechanical cutting means, one inlet conduit for introducing fluids, one outlet conduit for withdrawing fluids, resected tissue and debris, and one for an optical imaging means.

The mechanical cutting means comprises a plurality of thin longitudinal slits capable of forming elliptical blades in a unique configuration which are extensible and retractable. The blades are sheathed in the elongated cylindrical member along the longitudinal axis of the member. In an operational mode, the blades are extended to form elliptical shapes by a spring operated control means and, upon release of the spring, is retracted to a collapsed state.

Laser means are provided at the distal end portion of the elongated cylindrical member for producing and directing a laser beam into the adjacent tissue for coagulating at least a portion of it. An interstitial laser fiber for transmission of laser radiation is positioned concentrically within and beyond length of the rotatable shaft.

Automatic and manual drive mechanisms are connected to the rotating shaft to provide continuous or selective rotation of the cutting element. Advantageously, a pneumatic micromotor is used.

Other embodiments of the resectoscope include various optical imaging means that allow illumination, visualization and optionally recording of the procedure, and suction means to facilitate removal and retrieval of the resected tissue.

It is an object of this invention to provide an apparatus and a method of use which improves the efficiency and safety of a transurethral surgical procedure of the prostate.

It is a further object of this invention to provide a resectoscope which enables the resection of tissue by means of laser radiation which facilitates the retrieval of lased tissue for histological examination.

It is another object of this invention to provide a resectoscope which further has a laser for use in conjunction with the cutting means which penetrates the tissue to be cut and removed. The laser provides hemostasis at the site of the cutting, thereby reducing bleeding during the cutting procedure.

It is yet another object of the invention to provide extensible and retractable rotatable cutting members, which comprise a plurality of thin longitudinal slits which form elliptically shaped blades for resecting tissue.

It is a further object of the invention to provide a cutting means which can be manually or automatically utilized.

It is still a further object of the invention to provide a resectoscope utilizing a laser for coagulating tissue, mechanical cutting means for efficiently resecting the coagulated tissue, irrigation and suction means for effecting the irrigation of the operative situs where the resected tissue and irrigation liquid are removed and retrieved with the cellular structure preserved and suitable for viable histological examination.

BRIEF DESCRIPTION OF THE DRAWINGS

Other objects and many of the attendant advantages of this invention will be readily appreciated by reference to the following detailed description when considered in connection with the accompanying drawings wherein:

FIG. 1 is a front elevational view, partly in cross-section, of the resectoscope of the present invention;

FIG. 2 is an enlarged fragmentary cross-sectional view showing the mechanical cutting means sheathed in the elongated cylindrical member of the resectoscope of FIG. 1;

FIG. 3 is an enlarged fragmentary cross-sectional view showing the mechanical cutting means of the resectoscope of FIG. 1 shown in the operational extended mode;

DETAILED DESCRIPTION OF THE PREFERRED EMBODIMENT

Figure 4:
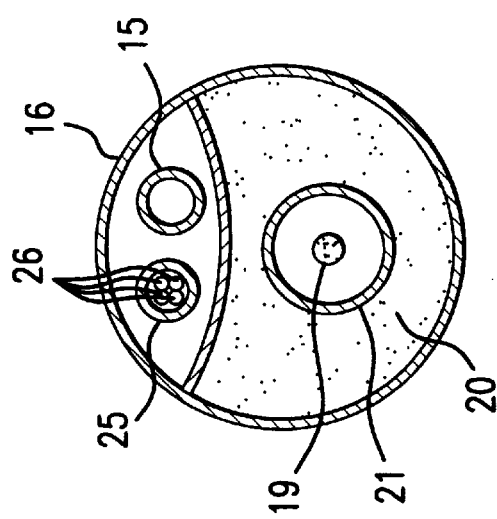
FIG. 4 is an enlarged cross-sectional view taken along line 4—4 of FIG. 1.
Figure 5:
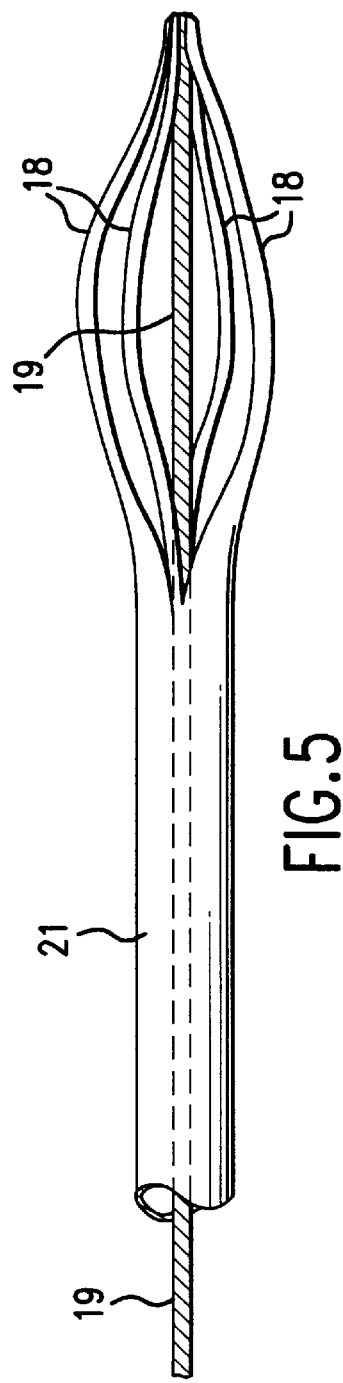
FIG. 5 is an enlarged fragmentary view of the rotatable shaft of the present invention with the elliptical blades in an open position and the laser delivery system concentric to the shaft.

Referring in greater detail to the various figures of the drawings wherein like reference characters refer to like parts, a resectoscope of the present invention is generally shown at 10 in FIG. 1.

The resectoscope 10 has an elongated cylindrical member 16 adapted to be inserted into the urethra for the purpose of performing prostate surgery as is well known in the art. The elongated cylindrical member 16, preferably made of stainless steel, extends along the entire length of resectoscope 10. As shown in FIGS. 1 and 4, the cylinder member 16 houses the working elements of the instrument. The resectoscope 10 has at least four conduits. An inlet conduit 15 is provided for the introduction of irrigating fluids and is connected to inlet port 14. The irrigating fluid is generally a saline solution. An outlet conduit 20 for withdrawing fluids, resected tissue and debris is connected to outlet port 22. Suction means (now shown) is connected to the outlet conduit 20 at the proximal end 13 of the elongated member 16 to facilitate removal and collection and retrieval of the resected tissue. A rotatable shaft 21 is also housed within cylindrical member 16, along with a laser delivery means 19 concentric within rotatable shaft 21.

Conduit 25 (FIG. 4) carries fiber optic filaments 26 for illumination and allows a viewing path of the procedure. Fiber optic filaments 26 are connected to a sight scope imaging means 11 near proximal end 13. The imaging means 11 has a side opening 12 to allow the entry of a light source to illuminate the procedure. Optionally, the scope of imaging means 11 can be connected to a camera and monitor which gives the surgeon the choice of viewing the procedure directly or through a monitor where the image can be projected. The scope means 11 and the fiber optic system includes prisms and lenses which are aligned to give the surgeon a thirty degree angle view of the procedure looking downward from the horizontal axis.

The novel configuration of the mechanical cutting means comprises a plurality of thin longitudinal slits to form sharp elliptical blades 18 which are resilient and are fully collapsible when sheathed in the distal end 17 of cylinder member 16 as shown in FIG. 2. As will be described in more detail, when activated, longitudinal blades 18 extend beyond distal end 17 of cylinder member 16, as shown in FIG. 3. Preferably, the blades 18 can be integral with the rotatable shaft 21. In one approach, the blades 18 can be formed by cutting longitudinal slits in the rotatable shaft 21 and then providing cutting edges to the slits. The mechanical cutting means 18 can also be attached by conventional fastening means such as with screws or by welding to the rotatable shaft 21.

Figure 6:
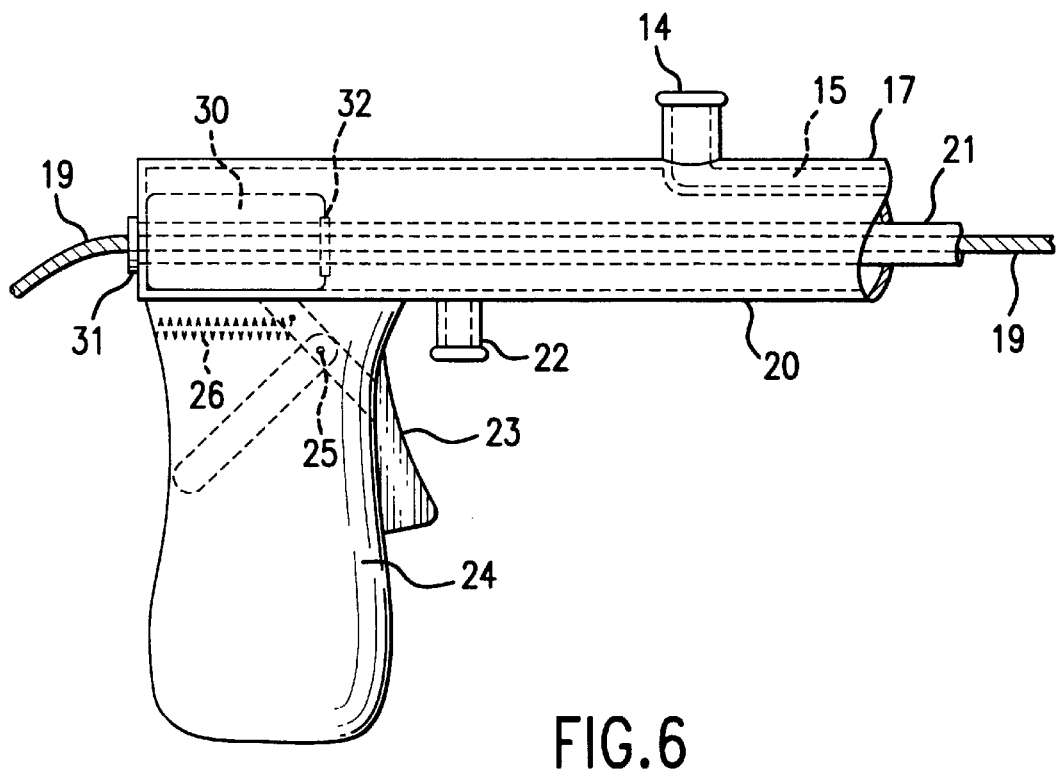
FIG. 6 is an elevational view, partly in phantom, showing the spring mechanism of the present invention for controlling the position of the various components.
Figure 7:
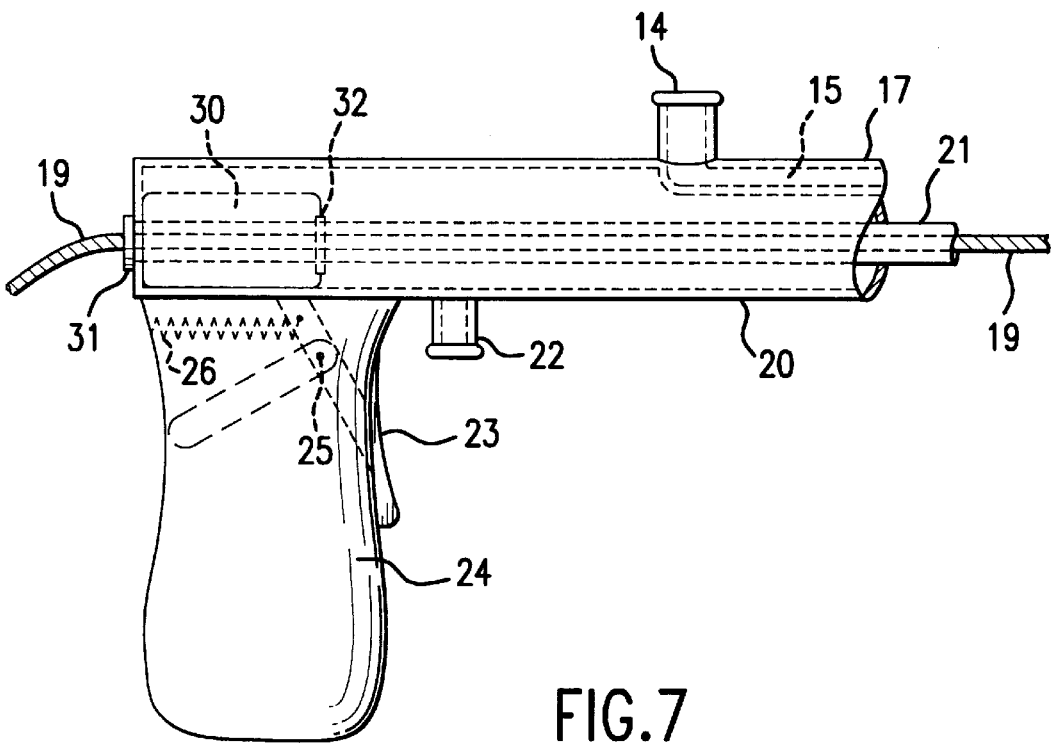
FIG. 7 is an elevational view, partly in phantom, showing the spring mechanism of the present invention in an activated position.

The mechanical cutting means 18 is connected to a drive mechanism 30 through rotatable shaft 21 which may rotate the cutting element either continuously or intermittently, manually or automatically. The drive mechanism 30 is preferably a pneumatic system such as is known in the medical art to run drills. While shown in simplified form in FIGS. 6 and 7, the specific construction and connection of such a drive system 30 to rotatable shaft 21 in order to rotate the shaft is well known to those skilled in the art and are not presented in detail. An elastomeric gasket 32 prevents irrigation fluid from entering into the drive housing. A gasket 31 prevents any fluid seepage from the back of resectoscope 10 and secures the interstitial laser fiber 19 to the instrument. A pistol-like hand grip 24 is attached to the resectoscope 10 near the pneumatic motor 30. The motor 30 is activated by trigger switch 23 located on hand grip 24. Trigger switch 23 controls the longitudinal movement of the motor 30 along the longitudinal axis of the elongated cylindrical member 16 by a lever mechanism 25 and a spring means 26. As a result, the rotatable shaft 21 connected to motor 30 is extended beyond the distal end portion 17 of the resectoscope 10 and the cutting blades 18 are unsheathed and opened. Simultaneously, the trigger mechanism activates the motor 30 and regulates the supply of air from a compressor (not shown). It should be understood that while a pneumatic drive is preferred, other means of rotating shaft 21 may also be used, such as an electric motor or manual means. The drive mechanism is not intended to be limited to any specific form. An air driven micromotor is preferred because it is more easily cleaned and sterilized. Releasing the trigger 23, the motor 30 and shaft 21 stop rotating and return to a position where the blades 18 become sheathed and in collapsed state. Alternatively, the resectoscope 10 may be fitted with a foot pedal to activate the drive means 30.

To more accurately control the rotation of the shaft 21, manual means such as a hand-operable pawl and ratchet-type drive mechanism may be provided in order to rotate shaft 21 independent of the rotation imparted by the pneumatic motor 30. A pawl and ratchet drive is not considered unique and construction of such a means for continuously, yet manually, rotating the shaft is well known to those skilled in the art and not discussed at length herein. Such manual control means is described in U.S. Pat. No. 5,201,731, which disclosure is incorporated by reference herein.

A laser delivery means 19 is connected to resectoscope 10 through elastomeric gasket 31 and motor 30 into shaft 21 and extends along the longitudinal axis of the shaft 21 through cutting means 18. The proximal end of the laser delivery means 19 is connected to a laser generator (not shown) which is provided with a foot control. The laser, when energized, assists in coagulating the tissue to stop or minimize the bleeding. At times during the resection procedure, the distance of the interstitial laser fiber 19 to the target tissue may need to be adjusted in order to control coagulation (as is known in the art). The distance is regulated simply by manually pushing or pulling the fiber 19 through gasket 31. The gasket 31 holds the fiber sufficiently tight such that once manipulation of the interstitial laser fiber 19 is complete, the fiber is secured firmly at the selected location within the shaft 21. Interstitial laser fiber 19 is attached to a laser generator (not shown) with a power of approximately 20 to 60 watts pulsed at approximately 20 to 30 seconds, or at a continuous mode for approximately 20 to 30 seconds.

To perform the resection of the prostate, the resectoscope 10 is inserted through the urethra toward the prostate. The tip of the fiber optic cable is inserted into the prostate core to a depth of approximately 5 centimeters. This will allow the uninsulated 2.5 centimeters of the tip to be well inside the core of the prostate. Once the fiber optic cable is powered with laser energy, this uninsulated 2.5 centimeter area will heat and coagulate the surrounding core of the prostate along a 360 degree path. Therefore, the core of the prostate tissue surrounding this 2.5 centimeter length will be coagulated for approximately 0.5 to 4 millimeters within the surrounding prostate tissue. The rotatable shaft 21 carrying the extensible and retractable mechanical cutting means 18 is connected to the drive means 30. Next, the interstitial laser fiber 19 is inserted through elastomeric gasket 31 along the longitudinal axis to connect with cutting elements 18. A laser feed cable (not shown) is connected with interstitial laser fiber 19 at proximal end 13 of the resectoscope. A saline fluid reservoir (not shown) is connected to inlet port 14. The outlet port 22 is connected to a suction machine (not shown) which provides continuous negative pressure in the area where the prostate is to be resected.

As the laser is energized, the target area is lased by interstitial fiber 19 within the prostatic tissue. The tissue is lased for approximately 20 to 30 seconds at pulsed or continuous mode. Then trigger 23 is squeezed toward handle 24, moving pneumatic motor 30 toward distal end 17 to expose cutting elements 18. The saline fluid and the suction machine are operated simultaneously so that the irrigation fluid, along with blood and cut tissue particles, are directed to the outlet port and out of instrument 10 to a collection means where the tissue particles can be collected for subsequent histological examination. According to the present invention, there is provided a method of interstitially lasing, coagulating, removing and retrieving prostate tissue of a living being utilizing the device of the invention. The said method comprises the steps of:

a) introducing elongated means having a distal end portion through the uretha of said being to a position adjacent to the prostate site:

b) coupling a rotatable shaft carrying a mechanical cutting means to said distal end portion of said elongated means;

c) coupling laser transmitting means to said distal end of said elongated means through said rotatable shaft;

d) proving a laser radiation source means for generating a laser beam coupled to said resectoscope by said laser transmitting means;

e) extending said rotatable cutting means and said laser transmitting means beyond the distal end of said elongated member invasively penetrating said prostate site;

f) interstitially lasing said prostate site to coagulate at least a portion of said tissue while preserving the cellular structure thereof;

g) activating said rotatable cutting means for engaging and cutting at least a portion of said coagulated tissue to produce resected particles while preserving the cellular structure thereof, said cellular structure being sufficiently preserved for histological examination; and h) carrying said particles out of the living being through said elongated means for retrieval.

Although the invention has been described with a certain degree of particularity, it is understood that the present disclosure has been made only by way of example and that numerous changes in the details of construction and the combination and arrangements of parts may be resorted to without departing from the spirit and scope of the invention.

What is claimed is:

1. A resectoscope for interstitially lasing, coagulating, cutting and removing prostate tissue of a living being, said resectoscope comprising:

a. an elongated cylindrical member having a longitudinal axis extending between a proximal and distal end of said cylindrical member, said distal end being introduced into a patient adjacent a prostate tissue site of the patient, said cylindrical member including inlet and outlet fluid conduits extending along said longitudinal axis for passage of irrigation fluid therethrough;

b. imaging means coupled to said cylindrical member for providing a visual image of the prostrate tissue site;

c. a longitudinally extended shaft rotatably mounted in said cylindrical member and having cutting blades disposed adjacent a distal end of said shaft, said rotatable shaft being displaceable along said longitudinal axis relative to said cylindrical member;

d. means for rotatably driving said shaft coupled to said cylindrical member; and, e. an interstitial laser delivery fiber extending concentrically through said shaft, said interstitial laser delivery fiber being selectively longitudinally displaceable relative to said shaft for extension thereof beyond said cutting blades.

2. The resectoscope as recited in claim 1 further comprising means for releasably maintaining a selected position of said interstitial laser delivery fiber relative to said shaft.

3. The resectoscope as recited in claim 1 wherein said shaft has a plurality of longitudinally directed slits formed adjacent said distal end thereof with sharpened edges to form said cutting blades.

4. The resectoscope as recited in claim 1 wherein said cutting blades are formed by resilient longitudinally extending elliptical blades.

5. The resectoscope as recited in claim 1 wherein said means for rotatably driving said shaft includes a motor disposed within said cylindrical member and drivingly coupled to said shaft, said motor being longitudinally displaceable within said cylindrical member.

6. The resectoscope as recited in claim 5 further comprising a handle coupled to said cylindrical member, a trigger switch coupled to said handle for activating said motor, and a lever mechanism coupled between said trigger switch and said motor for longitudinally displacing said motor and shaft.

7. The resectoscope as recited in claim 6 wherein said shaft has a plurality of longitudinally directed slits formed adjacent said distal end thereof with sharpened edges to form said cutting blades.

8. The resectoscope as recited in claim 6 wherein said cutting blades are formed by resilient longitudinally extending elliptical blades.

9. The resectoscope as recited in claim 6 further comprising means for releasably maintaining a selected position of said interstitial laser delivery fiber relative to said shaft.

10. A resectoscope for interstitially lasing, coagulating, cutting and removing prostate tissue of a living being, said resectoscope comprising:

a. an elongated cylindrical member having a longitudinal axis extending between a proximal and distal end of said cylindrical member, said distal end being introduced into a patient adjacent a prostate tissue site of the patient, said cylindrical member including inlet and outlet fluid conduits extending along said longitudinal axis for passage of irrigation fluid therethrough;

b. a handle coupled to said cylindrical member;

c. imaging means coupled to said cylindrical member for providing a visual image of the prostrate tissue site;

d. a longitudinally extended shaft rotatably mounted in said cylindrical member and having longitudinally extending cutting blades disposed adjacent a distal end of said shaft, said rotatable shaft being displaceable along said longitudinal axis relative to said cylindrical member;

e. means for rotatably driving said shaft coupled to said cylindrical member;

f. a trigger switch coupled to said handle for activating said rotatable driving means;

g. a lever mechanism coupled between said trigger switch and said rotatable driving means for longitudinally displacing said rotatable driving means and shaft coincident with said activation of said rotatable driving means; and, h. an interstitial laser delivery fiber extending concentrically through said shaft.

11. The resectoscope as recited in claim 10 wherein said interstitial laser delivery fiber is selectively longitudinally displaceable relative to said shaft for extension thereof beyond said cutting blades.

12. The resectoscope as recited in claim 11 further comprising means for releasably maintaining a selected position of said interstitial laser delivery fiber relative to said shaft.

13. A method of interstitially lasing, coagulating, and removing prostate tissue of a living being, comprising the steps of:

a. introducing a distal end portion of a cylindrical member into a patient adjacent a prostate tissue site;

b. providing a rotatably driven shaft with a cutting mechanism coupled thereto;

c. providing an interstitial laser delivery fiber extending concentrically through said shaft, said interstitial laser delivery fiber being displaceable relative to said shaft;

d. adjusting a distance between said interstitial laser delivery fiber and a portion of the patient's prostate tissue by selectively displacing said interstitial laser delivery fiber relative to said shaft;

e. coagulating the portion of the prostate tissue by irradiation with laser energy through said interstitial laser delivery fiber;

f. rotatably driving said cutting mechanism and displacing said cutting mechanism to the coagulated prostate tissue for excising at least a portion thereof; and, g. irrigating the prostate tissue site to remove the excised tissue therefrom.

* * * * *